United States Patent
Cekovic et al.

(10) Patent No.: US 12,246,080 B2
(45) Date of Patent: Mar. 11, 2025

(54) HIGH ACTIVE CONTENT COSMETIC SERUM COMPOSITION

(71) Applicant: L'OREAL, Paris (FR)

(72) Inventors: Rabije Cekovic, Staten Island, NY (US); Patricia Brieva, Manalapan, NJ (US)

(73) Assignee: L'OREAL, Paris (FR)

( * ) Notice: Subject to any disclaimer, the term of this patent is extended or adjusted under 35 U.S.C. 154(b) by 63 days.

(21) Appl. No.: 17/588,914

(22) Filed: Jan. 31, 2022

(65) Prior Publication Data

US 2023/0240957 A1     Aug. 3, 2023

(51) Int. Cl.
| | | |
|---|---|---|
| A61K 8/42 | (2006.01) | |
| A61K 8/44 | (2006.01) | |
| A61Q 19/00 | (2006.01) | |

(52) U.S. Cl.
CPC ............ *A61K 8/44* (2013.01); *A61K 8/42* (2013.01); *A61Q 19/00* (2013.01)

(58) Field of Classification Search
CPC . A61K 8/44; A61K 8/42; A61K 8/345; A61K 8/69; A61Q 19/00; A61Q 19/08; A61Q 19/10
IPC ............... A61K 8/44,8/42, 8/69; A61Q 19/00
See application file for complete search history.

(56) References Cited

U.S. PATENT DOCUMENTS

| | | | |
|---|---|---|---|
| 6,884,425 B2 | 4/2005 | Breton et al. | |
| 7,125,559 B2 | 10/2006 | Breton | |
| 10,449,133 B1 * | 10/2019 | Faig | A61K 8/34 |
| 10,660,420 B2 * | 5/2020 | Shah | A61K 8/8129 |
| 2008/0014230 A1 | 1/2008 | Pineau et al. | |
| 2014/0107059 A1 * | 4/2014 | Pan | A61K 8/4953 |
| | | | 514/46 |
| 2015/0335560 A1 * | 11/2015 | Bernard | A61K 8/375 |
| | | | 514/786 |

FOREIGN PATENT DOCUMENTS

| | | |
|---|---|---|
| FR | 2895256 | 6/2007 |
| FR | 2897776 | 8/2007 |
| WO | 2020041389 A1 | 2/2020 |
| WO | 2020254645 | 12/2020 |

OTHER PUBLICATIONS

Search Report issued for counterpart French Application No. FR 2202300 dated Nov. 9, 2022.

* cited by examiner

*Primary Examiner* — Trevor Love
*Assistant Examiner* — Janet Joseph
(74) *Attorney, Agent, or Firm* — McNees Wallace & Nurick LLC

(57) ABSTRACT

A water-based composition in a cosmetically acceptable carrier that includes acetyl trifluoromethylphenyl valylglycine stabilized by inclusion of hydroxyethyl urea in the absence of other solvents. The composition is stable as evidenced by a lack of crystal formation that is visible to the naked eye, and a lack of visually perceptible crystal formation at an ambient temperature from about 25° C. up to about 37° C. and after 10 days of freeze thaw cycles from −20° C. through 20° C.

20 Claims, No Drawings

HIGH ACTIVE CONTENT COSMETIC SERUM COMPOSITION

FIELD

The present disclosure is directed to skin care compositions that include high amounts of skin actives, including together with one or more additional actives including but not limited to antioxidants. In particular, the compositions include acetyl trifluoromethylphenyl valylglycine and to methods for solubilizing it with a hydroxyethyl urea stabilizer which prevents crystallization of the acetyl trifluoromethylphenyl valylglycine and/or other actives to preserve the benefits of the actives to keratinous tissues, for example skin.

BACKGROUND OF THE INVENTION

Products for treating skin typically include active compounds, but many active compounds present challenges with respect to solubility, stability, and/or maintained effectiveness, particularly over time and over a wide temperature range of storage or use. It is known, in particular, that certain actives such as N-acylamino amide compounds, including, for example, acetyl trifluoromethylphenyl valylglycine, are difficult to stabilize even at low concentrations in order to maintain activity over a typical product shelf life.

In some examples, there are anhydrous compositions disclosed in the art that include acetyl trifluoromethylphenyl valylglycine at relatively high concentrations in the presence of one, two, or more solubilizing solvents, such as ethoxydiglycol, dimethyl isosorbide, triethyl citrate, isopropyl lauryl sarcosinate, and propylene glycol, however, such compositions do not necessarily provide a cosmetic carrier system that meets the needs of a consumer, particularly for a leave on composition or one that includes water soluble actives and other ingredients that are not compatible with an essentially anhydrous carrier system. Thus, there remains a need to deliver higher amounts of—acylamino amide compounds, including, for example, acetyl trifluoromethylphenyl valylglycine actives in order to meet consumer expectations for effectiveness.

BRIEF SUMMARY

The inventors have provided a solution to the shortcomings in the art as mentioned above, the solution comprising a cosmetic composition that includes a high concentration of acetyl trifluoromethylphenyl valylglycine along with other optional actives stabilized in a water-based carrier system.

In a first embodiment, the disclosure provides a composition that includes:
  (a) acetyl trifluoromethylphenyl valylglycine, present from about 0.5% and up to about 2%;
  (b) hydroxyethyl urea present from about 4.5% to about 18%;
  (c) a cosmetically acceptable carrier comprising water; and
  (d) optionally, one or more additives
  wherein all weight percentages are based on the total weight of the cosmetic composition.

In some embodiments, the composition demonstrates stability as evidenced by a lack of crystal formation that is visible to the naked eye, and a lack of visually perceptible crystal formation at an ambient temperature from about 25° C. up to about 37° C. after freeze thaw cycles from −20° C. through 20° C. over a period of 10 days.

In some embodiments the composition may demonstrate stability when crystals are visualized at a temperature at or below 4° C., such crystals disappear with or without mild agitation within 24 hours of reaching an ambient temperature from about 25° C. up to about 37° C., or after freeze thaw cycles from −20° C. through 20° C., or from −15° C. through 25° C. In some embodiments, the composition may demonstrate stability for a period of time up to eight (8) weeks.

In various embodiments, the composition has a pH in a range from about 4.5 to about 6.5. In some particular embodiments, the composition has a pH of about 4.7 to about 5 wherein the acetyl trifluoromethylphenyl valylglycine is present from about 0.5% to about 1%. In some particular embodiments, the composition has a pH of about 6 wherein the acetyl trifluoromethylphenyl valylglycine is present over about 1% and up to about 2% or less than 2%. In various embodiments, the pH may be adjusted by inclusion of the hydroxyethyl urea and addition of pH adjusters, for example but not limited to potassium hydroxide.

In some particular embodiments, the disclosure provides a composition that includes:
  (a) acetyl trifluoromethylphenyl valylglycine, present at about 1%;
  (b) hydroxyethyl urea present at about 23%;
  (c) a cosmetically acceptable carrier comprising water; and
  (d) optionally, one or more additives
  wherein the composition has a pH in a range from about 4.7 to about 5, and wherein all weight percentages are based on the total weight of the cosmetic composition.

In some particular embodiments, the disclosure provides a composition that includes;
  (a) the acetyl trifluoromethylphenyl valylglycine present at about 2%, by weight of the composition;
  (b) the hydroxyethyl urea present from about 4.5% to about 11.7%, by weight of the composition;
  (c) the cosmetically acceptable carrier present from about 30% to about 70%, by weight of the composition; and
  (d) the other optional ingredients present from about 0.001% to about 20%, by weight of the composition.

In some embodiments, water is present from about 10% to about 75%, by weight of the composition.

In some embodiments, the composition also includes one or more additives, selected from the group consisting of fatty compound(s); thickening agent(s); surfactants; other additives and skin active agent(s); and combinations of the foregoing.

In some embodiments, the optionally one or more additives is selected from the group consisting of pH adjusters, chelating agents, skin care actives, preservatives, fillers, powders, fragrances, dyes, pigments, and combinations thereof.

In some embodiments, the optional one or more additives is selected from the group consisting of ethylhexylglycerin, pentylene glycol, carbomer, methyl gluceth-20, Bis-PEG-18 methyl ether dimethyl silane, sodium benzoate, sodium hydroxide, phenoxyethanol, taurine, adenosine, hydroxyethylpiperazine ethane sulfonic acid, niacinamide, and combinations thereof. In some embodiments, the optional one or more additives comprises each of ethylhexylglycerin, pentylene glycol, carbomer, methyl gluceth-20, Bis-PEG-18 methyl ether dimethyl silane, sodium benzoate, sodium hydroxide, phenoxyethanol, taurine, adenosine, hydroxyethylpiperazine ethane sulfonic acid, and niacinamide.

In some embodiments, the composition is monophasic and essentially free of oil.

In some embodiments, the composition includes at least one of a humectant or surfactant or a water dispersible silicone. In some embodiments, the composition includes at least one of methyl gluceth-20, and Bis-PEG-18 methyl ether dimethyl silane.

In some embodiments, the composition excludes one or more ingredients selected from the group consisting of water-soluble solvents selected from the group consisting of monoalcohols and polyols, diols, glycols, glycol ethers and combinations thereof.

In some embodiments, the composition excludes one or more ingredients selected from the group consisting of ethoxydiglycol, dimethyl isosorbide, triethyl citrate, isopropyl lauryl sarcosinate, propylene glycol, propanediol, and combinations thereof.

In some embodiments, the composition excludes or is essentially free from ingredients selected from the group consisting of parabens, phthalates, cyclomethicones, fragrance, silicone, mineral oil, synthetic dyes, gelling agents, sulfates, polyquaternium, microplastics, EDTA, silicone oils, mineral UV filter agents, organic UV filter agents, and combinations thereof.

In some embodiments, the composition may include only nominal amounts of petrol based ingredients or may be free from petrol based ingredients.

In some particular embodiments, the disclosure provides a composition that:
(a) acetyl trifluoromethylphenyl valylglycine, present at about 2%;
(b) hydroxyethyl urea present from about 4.5% to about 18%;
(c) a cosmetically acceptable carrier comprising water; and
(d) optionally, one or more additives
wherein all weight percentages are based on the total weight of the cosmetic composition, and wherein the composition demonstrates stability as evidenced by a lack of crystal formation that is visible to the naked eye, and a lack of visually perceptible crystal formation at an ambient temperature from about 25° C. up to about 37° C. and after 10 days of freeze thaw cycles from −20° C. through 20° C., and wherein the composition excludes one or more ingredients selected from the group consisting of ethoxydiglycol, dimethyl isosorbide, triethyl citrate, isopropyl lauryl sarcosinate, propylene glycol, propanediol, or combinations thereof. In some embodiments the composition may demonstrate stability when crystals are visualized at a temperature at or below 4° C., such crystals disappear with or without mild agitation within 24 hours of reaching an ambient temperature from about 25° C. up to about 37° C., or after freeze thaw cycles from −20° C. through 20° C., or from −15° C. through 25° C. In some embodiments, the composition may demonstrate stability for a period of time up to eight (8) weeks.

In some particular embodiments, the disclosure provides a composition that:
(a) acetyl trifluoromethylphenyl valylglycine, present at about 2%;
(b) hydroxyethyl urea present from about 4.5% to about 18%;
(c) a cosmetically acceptable carrier comprising water; and
(d) optionally, one or more additives comprising methyl gluceth-20 or Bis-PEG-18 methyl ether dimethyl silane
wherein all weight percentages are based on the total weight of the cosmetic composition, and wherein the composition demonstrates stability as evidenced by a lack of crystal formation that is visible to the naked eye, and a lack of visually perceptible crystal formation at an ambient temperature from about 25° C. up to about 37° C. and after 10 days of freeze thaw cycles from −20° C. through 20° C., and wherein the composition excludes one or more ingredients selected from the group consisting of ethoxydiglycol, dimethyl isosorbide, triethyl citrate, isopropyl lauryl sarcosinate, propylene glycol, propanediol, or combinations thereof. In some embodiments the composition may demonstrate stability when crystals are visualized at a temperature at or below 4° C., such crystals disappear with or without mild agitation within 24 hours of reaching an ambient temperature from about 25° C. up to about 37° C., or after freeze thaw cycles from −20° C. through 20° C., or from −15° C. through 25° C. In some embodiments, the composition may demonstrate stability for a period of time up to eight (8) weeks.

In another embodiment, the disclosure provides methods of preparing the inventive composition, and methods of providing skin care by applying the inventive composition to skin.

These and other aspects of the invention are set out in the appended claims and described in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

In the present application, the terms "keratinous substrate" and "keratinous tissue" each includes but is not limited to skin, hair, and nails.

The term "cosmetically acceptable carrier" means a carrier that is compatible with any keratinous substrate, and for purposes hereof, includes water and optionally water based solvents subject to any exclusions as disclosed herein.

As used herein, the term "serum" refers to a hydrophilic liquid composition formulated for topical application. A serum may optionally be free from or essentially free from one or more of an oil, including an emollient, a wax and a silicone oil.

The terms "stable" and "stability" as used in reference to the disclosed composition means that the composition lacks crystal formation that is visible to the naked eye, and does not demonstrate visually perceptible crystal formation over a period of time, for example for one, two or four or five days, or for a period of one or more weeks, and for example up to eight (8) weeks. In some examples, when crystals are visualized at a temperature at or below 4° C., such crystals disappear with or without mild agitation within 24 hours of reaching an ambient temperature from about 25° C. up to about 37° C. and after freeze thaw cycles from −20° C. through 20° C. The exemplified embodiments of the inventive composition shown in the examples herein demonstrated stability an ambient temperature from about 25° C. up to about 37° C. after freeze thaw cycles over a period of 10 days from −20° C. through 20° C. In some embodiments the composition may demonstrate stability when crystals are visualized at a temperature at or below 4° C., such crystals disappear with or without mild agitation within 24 hours of reaching an ambient temperature from about 25° C. up to about 37° C., or after freeze thaw cycles from −20° C. through 20° C., or from −15° C. through 25° C. In some embodiments, the composition may demonstrate stability for a period of time up to eight (8) weeks.

The limited solubility of acetyl trifluoromethylphenyl valylglycine has presented challenges for its use in cosmetic products, in particular those in which high amounts of actives are desirable. Provided herein is an inventive composition in the context of a cosmetically acceptable carrier wherein acetyl trifluoromethylphenyl valylglycine is formulated to be stabilized by inclusion of hydroxyethyl urea. As further described herein and as exemplified in the non-limiting examples, the hydroxyethyl urea provides stabilization at a range of concentrations to enable inclusion of acetyl trifluoromethylphenyl valylglycine as at least one active in amounts from about 0.5% and up to about 2% and the hydroxyethyl urea is present from about from about 4% to less than 27%, or from about 4% to about 26.5%, or from about 4.5% and up to about 25%, or from about 4.5% and up to about 23.4%, or from about 4.5% to about 18%, or from about 4.5% to about 17.55%, or from about 4.5% to about 11.7%, or from about 11.7% to about 23.4%, or from about 11.7% to about 18%, all amounts by weight of the composition.

The inventors have provided a composition in which the combination of acetyl trifluoromethylphenyl valylglycine with hydroxyethyl urea enables stable solubilization and storage of a cosmetical composition with relatively high amounts acetyl trifluoromethylphenyl valylglycine.

In various embodiments, the composition has a pH in a range from about 4.5 to about 6.5. In some particular embodiments, the composition has a pH of about 4.7 to about 5 wherein the acetyl trifluoromethylphenyl valylglycine is present from about 0.5% to about 1%. In some such embodiments, the hydroxyethyl urea is present at a concentration in a range of about 18% to about 30%, and in one example the hydroxyethyl urea is present at a concentration less than about 27% wherein the pH may be adjusted using a pH adjuster. In some particular embodiments, the composition has a pH of about 6 wherein the acetyl trifluoromethylphenyl valylglycine is present over about 1% and up to about 2% or less than 2%. In some such embodiments, the hydroxyethyl urea is present at a concentration in a range of about 18% to about 30%, and in one example the hydroxyethyl urea is present at a concentration in a range from about 4.5% to about 23.4% wherein the pH may be adjusted using a pH adjuster. In various embodiments, the pH may be adjusted by inclusion of the hydroxyethyl urea and addition of pH adjusters, for example but not limited to potassium hydroxide.

In some such embodiments, the hydroxyethyl urea is present at a concentration in a range of about 18% to about 30%, and in one example the hydroxyethyl urea is present at a concentration of about 23% wherein the pH may be adjusted using a pH adjuster.

In some particular embodiments, the composition does not include any one or more of ethoxydiglycol, dimethyl isosorbide, triethyl citrate, isopropyl lauryl sarcosinate, propylene glycol, propanediol, In various embodiments, the disclosure provides a composition that includes:
(a) acetyl trifluoromethylphenyl valylglycine, present from about 0.5% and up to about 2%;
(b) hydroxyethyl urea present from about 4% and up to about 26.5% and less than 27%;
(c) water; and
(d) optionally, one or more additives,
wherein all weight percentages are based on the total weight of the cosmetic composition.

The cosmetic composition may optionally include additional ingredients selected from the group consisting of water-soluble solvents that exclude ethoxydiglycol, dimethyl isosorbide, triethyl citrate, isopropyl lauryl sarcosinate, propylene glycol, propanediol, or combinations thereof; fatty compound(s); thickening agent(s); other ingredients and skin active agent(s); and combinations of the foregoing.

N-Acylamino Amide

In accordance with the various embodiments, an N-acylamino amide, and in more particular embodiments, acetyl trifluoromethylphenyl valylglycine, is present in the inventive composition. In the various embodiments, the acetyl trifluoromethylphenyl valylglycine is present in a range from about 0.5% and up to about 2% by weight of the composition.

Referring to U.S. Pat. No. 6,987,128, which claims priority to FR0007344A, the entireties of which are incorporated herein by reference, a novel family of compounds of the N-acylamino-amide family were disclosed for use on body or face skin to address the effects of ageing, whether chronobiologic or light-induced, and in particular skin ageing caused by decrease of skin elasticity and/or by collagen degradation in the structure of tissues.

The inventive composition hereof includes use of a compound of the N-acylamino-amide family, in some specific and exemplified embodiments, acetyl trifluoromethylphenyl valylglycine, present in a range from about 0.5% and up to about 2% by weight of the composition.

Thus, in various embodiments, the compound of the N-acylamino-amide family, in some specific and exemplified embodiments, acetyl trifluoromethylphenyl valylglycine is present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, to about 2.0 percent, including increments and ranges therein and there between.

Hydroxyethyl Urea

In accordance with the various embodiments, hydroxyethyl urea is present in the inventive composition. In some embodiments, the composition does not include any derivative of hydroxyethyl urea, or urea or any derivative of urea that is not hydroxyethyl urea.

In the various embodiments, hydroxyethyl urea is present in a range from about 4% to less than 27%, by weight of the composition, or from about 4% to about 26.5%, or from about 4.5% and up to about 25%, or from about 4.5% and up to about 23.4%, or from about 4.5% to about 18%, or from about 4.5% to about 17.55%, or from about 4.5% to about 11.7%, or from about 11.7% to about 23.4%, or from about 11.7% to about 18%. In some embodiments, the hydroxyethyl urea is present in the composition from about 4% to about 5%, or from about 11% to about 12%, or from about 17% to about 18.5%, or from about 22% to about 25%, or any suitable combination, sub-combination, range, or sub-range thereof by weight, based on the weight of the composition. One of ordinary skill in the art, however, will appreciate that other ranges are within the scope of the invention.

As exemplified herein, hydroxyethyl urea is provided in a raw material that has a concentration of hydroxyethyl urea active at about 45%, by weight of the raw material.

Thus, in various embodiments, the hydroxyethyl urea is present by weight, based on the total weight of the composition, from about 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, to about 26.5 percent and less than 27 percent, including increments and ranges therein and there between.

Cosmetically Acceptable Carrier

In accordance with the various embodiments, the compositions include a cosmetically acceptable carrier. The total amount of the cosmetically acceptable carrier in compositions may be from about 30% to about 70%, based on the total weight of the composition. Thus, the cosmetically acceptable carrier is present, by weight, based on the total weight of the composition, from about 30, 40, 45, 50, 55, 60, 65, to about 70 percent, by weight, including increments and ranges therein and there between. One of ordinary skill in the art, however, will appreciate that other ranges are within the scope of the invention.

The cosmetically acceptable carrier includes water present in a range from about 10% to about 80%, and in some embodiments, from about 20% to about 75%, and in some embodiments, from about 30% to about 70%, and in some embodiments, from about 45% to % or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 20, 25, 30, 35, 40, 45, 50, 55, 60, 65, 70, 75, 80 to about 90 percent, by weight, including increments and ranges therein and there between. One of ordinary skill in the art, however, will appreciate that other ranges are within the scope of the invention.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition, in particular the water phase of the composition, may be adjusted prior to combining the oil phase with the water phase to avoid the practical difficulty with measuring pH in an internal water phase of the water-in-oil emulsion. In various embodiments, the pH is a physiologically acceptable pH. In some embodiments, the pH of the water phase prior to emulsification can be adjusted with pH adjusters to a pH in a range from about 3 to about 9, or from about 5 to about 7.5 by addition of a base (organic or inorganic) to the composition, for example sodium hydroxide, ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

The cosmetically acceptable carrier can include in addition to water, water-soluble solvents. In some embodiments that may include water-soluble solvents, the composition is nevertheless free of and does not include or is free of any one or more of ethoxydiglycol, dimethyl isosorbide, triethyl citrate, isopropyl lauryl sarcosinate, propylene glycol, propanediol, or combinations thereof. In some particular embodiments, the composition does not include or is free of at least one or more of water-soluble solvents selected from the group consisting of monoalcohols and polyols, diols, glycols, glycol ethers and combinations thereof.

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, C1-30, C1-15, C1-10, or C1-4 alcohols), organic solvents, polyols (polyhydric alcohols), glycols (e.g., butylene glycol, caprylyl glycol, etc.), and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the disclosure include one or more glycols and/or one or more alcohols, for example, one or more water-soluble solvents selected from the group consisting of butylene glycol, caprylyl glycol, propanediol, glycerin, and a mixture thereof.

The total amount of the one or more water-soluble solvents can vary but is typically about 1 to about 40% by weight, based on the total weight of the cosmetic composition. In some cases, the total amount of the one or more water-soluble solvents is about 1 to about 35% by weight, about 1 to about 30% by weight, about 1 to about 25% by weight, about 2 to about 40% by weight, about 2 to about 35% by weight, about 2 to about 30% by weight, about 2 to about 25% by weight, about 5 to about 40% by weight, about 5 to about 35% by weight, about 5 to about 30% by weight, about 5 to about 25% by weight, about 10 to about 40% by weight, about 10 to about 35% by weight, about 10 to about 30% by weight, about 10 to about 25% by weight, about 15 to about 40% by weight, about 15 to about 35% by weight, about 15 to about 30% by weight, or about 15 to about 25% by weight, based on the total weight of the cosmetic composition.

Non-Silicone Fatty Compounds

In various embodiments, the composition may include one or more fatty compounds. In some embodiments the compounds may be non-silicone fatty compounds, or silicone compounds. In some embodiments the composition is free from one or more fatty compounds selected from the group consisting of on-silicone fatty compounds, or silicone compounds.

The cosmetic composition may include one or more non-silicone fatty compounds. The term "non-silicone fatty compound" means a fatty compound that does not containing any silicon atoms (Si). Non-limiting examples of non-silicone fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

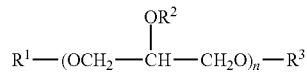

wherein the average value of n is about 3 and R1, R2 and R3 each may independently be a fatty acid moiety or hydrogen, provided that at least one of R1, R2, and R3 is a fatty acid moiety. For instance, R1, R2 and R3 may be saturated or unsaturated, straight or branched, and have a length of C1-C40, C1-C30, C1-C25, or C1-C20, C1-C16, or C1-C10. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Non-limiting examples of the high melting point compounds are found in the International Cosmetic Ingredient Dictionary, Sixteenth Edition, 2016, which is incorporated by reference herein in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distributions in which the main alkyl chain is cetyl, stearyl or behenyl groups. In the present application, more preferred fatty alcohols are cetyl alcohol, stearyl alcohol and mixtures thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

Mention may be made, among the waxes capable of being used as non-silicone fatty compounds, of animal waxes, such as beeswax; vegetable waxes, such as sunflower seed (*Helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as C12-C15 alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, C10-C18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The total amount of non-silicone fatty compounds in the cosmetic compositions may vary, and the total amount of fatty compounds may be about 5 to about 85% by weight, based on the total weight of the cosmetic composition. In some cases, the total amount of the non-silicone fatty compounds. In some cases, the total amount of fatty compounds may be about 5 to about 80% by weight, or about 5 to about 75 wt., based on the total weight of the cosmetic composition.

For instance, the total amount of non-silicone fatty compounds may be about 30 to about 85% by weight, about 40 to about 85% by weight, about 50 to about 85% by weight, about 60 to about 85% by weight, about 30 to about 80% by weight, about 40 to about 80% by weight, about 50 to about 80% by weight, or about 60 to about 80% by weight, based on the total weight of the cosmetic composition.

Cosmetic compositions that include water will often include lower amounts of total non-silicone fatty compounds. For instance, the total amount of non-silicone fatty compounds may be about 1 to about 60% by weight, about 1 to about 50% by weight, about 1 to about 40% by weight, about 1 to about 30% by weight, about 5 to about 60% by weight, about 5 to about 50% by weight, about 5 to about 40% by weight, or about 5 to about 30% by weight, based on the total weight of the cosmetic composition.

Thickening Agents

The one or more thickening agents may be carbomer, xanthan gum, guar gum, biosaccharide gum, cellulose, acacia Seneca gum, *sclerotium* gum, agarose, pectin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerythritol. The carbomers are available as the CARBOPOL 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerythritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of thickening agent(s), when present, may vary but is typically about 0.01 to about 5% by weight, based on the total weight of the cosmetic compositions. Similarly, the total amount of thickening agent(s) may be about 0.01 to about 4% by weight, about 0.01 to about 3% by weight, about 0.1 to about 5% by weight, about 0.1 to about 4% by weight, about 0.1 to about 3% by weight, about 0.5 to about 5% by weight, about 0.5 to about 4% by weight, about 0.5 to about 3% by weight, based on the total weight of the cosmetic composition.

Skin Active Ingredients

The cosmetic compositions described herein may include one or more skin active ingredients. Non-limiting examples skin active agents include adenosine, 2-[4-(2-hydroxyethyl) piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the skin active ingredient is adenosine.

In one embodiment, the cosmetic compositions include a skin active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of Imperata cylindra sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-0 ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the *aloe* family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-0 ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the α-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the cosmetic composition comprises a skin active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha* pipenta 25 *Rosmarinus officinalis, Salvia officinalis* and *Thymus vulgaris*, all marketed for example by Maruzen— extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech;— extracts of *Pygeum* afrianum such as that sold under the name *Pygeum* afrianum sterolic lipid extract by Euromed—extracts of *Serenoa serrulata* such as those sold under the name Viapure *Sabal* by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of 'meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark succirubra such as that sold under the name Red Bark HS by Alban Muller—extracts of Quillaja *saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20-phthalimidoperoxyhexanoic acid-citrate tri (C12-C13) sold under the name COSMACOL® ECI by Sasol; trialkyl citrate (C14-C15) sold under the name COSMACOL® ECL by Sasol-10-hydroxydecanoic acid, including mixtures acid-hydroxydecanoic October 25, sebacic acid and 1,10-decandiol such as that sold under the name Acnacidol BG by Vincience and mixtures thereof.

The cosmetic compositions may include 10 ppm to 10% by weight (100,000 ppm), 10 ppm to 5% by weight (50,000 ppm), 10 ppm to 2.5% by weight (25,000 ppm), 10 ppm to 1% by weight (10,000 ppm), 10 ppm to 0.5% by weight (5,000 ppm), 10 ppm to 0.1% by weight (1,000 ppm), or 10 ppm to 500 ppm of one or more skin active ingredients. In some cases, the one or more skin active ingredients is present in an amount from 10, 20, 30, 40, 50, 60, 70, 80, 90, 100, 150, or 200 ppm to 500, 600, 700, 800, 900, 0.1% by weight (1000 ppm), 0.5% by weight (5,000 ppm), 1% by weight (10,000 ppm)), 5% by weight (50,000 ppm), or 10% by weight (100,000 ppm).

Optional Additives

The compositions can also comprise at least one additive used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, vitamins, panthenol, silicones, gelling agents, odor absorbers, and colorants. Additives used according to the disclosure may be selected from actives, including but not limited to: anti-microbial components, including, but not limited to, capryloyl glycine and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example *Pyrus Malus* (Apple) Fruit Extract, and *Aloe Barbadensis* Leaf Juice Powder; citric acid, sodium chloride; acetyl trifluoromethylphenyl valylglycine and combinations thereof. Although the optional active additives are given as examples, it will be appreciated that other optional components compatible with cosmetic applications known in the art may be used.

Also, in accordance with the disclosure, in some embodiments, there may be one or more other cosmetically acceptable additives present in the cosmetic composition. In some embodiments, cosmetically acceptable additives used according to the disclosure may be selected from colorants, preservatives, fragrances, dyes, neutralizing or pH-adjusting agents (e.g., triethylamine (TEA), sodium hydroxide, citric acid, and hydrochloric acid). Although the optional additives are given as examples, it will be appreciated that other optional components compatible with cosmetic applications known in the art may be used.

In accordance with the various embodiments, the amount of one or more actives and additives, alone or in combination, present in the composition can be present in the composition according to the disclosure in a range from less than about 0.001%, or from about 0.001% to about 20%, by weight, or from about 0.005% to about 0.01%, or from about 0.01% to about 0.1%, or from about 0.15% to about 5%, or from about 0.40% to about 4%, or from about 0.5% to about 2% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Optional Additional Antioxidants

In accordance with the various embodiments, compositions may contain one or more antioxidants. Additional antioxidants can be any antioxidant suitable for use in cosmetic formulations. Suitable antioxidants include, but are not limited to, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as Vitamin E), vitamin A, co-enzyme Q10, bioflavonoids, glutathione, plant extracts (such as rosemary extract, olive leaf extracts), and green tea extracts, lignans, and aurones. In some embodiments, the antioxidants are selected from the group consisting of sodium tetracarboxymethylchalcone, glycosyl hesperidin, hesperetin, hesperidine, silymarin, taxifolin, apigenin, baicalein, baicalin, luteolin, quercetin, hydroxycinnamate, ferulic acid, oryzanol, p-coumaric acid, mangiferin and combinations thereof.

The amount of antioxidants, if any, present in the compositions can range from about 0.01% to about 20%, or from about 0.1% to about 20%, or from about 0.01% to about 2%, based on the total weight of the composition.

In some examples of the composition comprising additional ingredients, the composition may comprise at least one additive selected from the group consisting of humectants, surfactants, water dispersible silicones, pH adjusters, chelating agents, skin care actives, preservatives, fillers, powders, fragrances, dyes, pigments, and combinations thereof.

In some examples of the composition comprising additional ingredients, the composition may comprise at least one additive used in the cosmetics field which does not affect the properties of the compositions according to the invention, such as humectants or surfactants (for example methyl gluceth-20), silicones or water dispersible silicones (for example Bis-PEG-18 methyl ether dimethyl silane), fragrances, preservatives/anti-microbials (for example, chlorphenesin, salicylic acid, phenoxyethanol, potassium sorbate, and caprylyl glycol); actives (for example, hydroxyacetophenone, vitamins, panthenol, tocopherol); oil-soluble active ingredients (for example, vitamin A, beta carotene, tocopherol/vitamin E) and emollients; coloring materials/pigments; essential oils; antioxidants; hydroxy acids; citric acid, sodium citrate, sodium chloride; neutralizing, chelating or pH-adjusting agents (for example, triethylamine (TEA), trisodium ethylenediamine disuccinate, EDTA, and sodium hydroxide), and combinations thereof. In some particular examples, the composition may comprise together with at least one fatty compound oil soluble actives selected from the group consisting of vitamin E, vitamin A, beta carotene, retinol, resveratrol, derivatives thereof, and combinations thereof. And in some particular examples, composition may comprise water soluble actives selected from the group consisting of vitamin C, niacinamide, derivatives thereof, and combinations thereof.

In some examples of the composition comprising additional ingredients, the composition includes at last one ingredient selected from the group consisting of ethylhexylglycerin, pentylene glycol, carbomer, methyl gluceth-20, Bis-PEG-18 methyl ether dimethyl silane, sodium benzoate, sodium hydroxide, phenoxyethanol, taurine, adenosine, hydroxyethylpiperazine ethane sulfonic acid, niacinamide and combinations thereof.

In some examples of the composition comprising additional ingredients, the composition includes each of ethylhexylglycerin, pentylene glycol, carbomer, methyl gluceth-20, Bis-PEG-18 methyl ether dimethyl silane, sodium benzoate, sodium hydroxide, phenoxyethanol, taurine, adenosine, hydroxyethylpiperazine ethane sulfonic acid, and niacinamide.

In some examples of the composition comprising additional ingredients, the composition includes ethylhexylglycerin (about 0.10% by weight), pentylene glycol (about 1.00% by weight), carbomer (about 0.40% by weight), methyl gluceth-20 (about 2.00% by weight), sodium benzoate (about 0.30% by weight), sodium hydroxide (about 0.30% by weight), phenoxyethanol (about 0.70% by weight), taurine (about 3.00% by weight), adenosine (about 0.04% by weight), hydroxyethylpiperazine ethane sulfonic acid (about 5.00% by weight), niacinamide (about 5.00% by weight), and water (about 30-45% by weight).

In some examples of the composition comprising additional ingredients, the composition includes ethylhexylglycerin (about 0.10% by weight), pentylene glycol (about 1.00% by weight), carbomer (about 0.30% by weight), Bis-PEG-18 methyl ether dimethyl silane (about 2.00% by weight), sodium benzoate (about 0.30% by weight), sodium hydroxide (about 0.35% by weight), phenoxyethanol (about 0.70% by weight), taurine (about 1.50% by weight), adenosine (about 0.04% by weight), hydroxyethylpiperazine ethane sulfonic acid (about 5.00% by weight), niacinamide (about 5.00% by weight), and water (about 30-45% by weight).

Although the optional additives are given as examples, it will be appreciated that other optional components compatible with cosmetic applications known in the art may be used that are suitable for a cosmetic composition.

In accordance with the various embodiments, the amount of one or more actives and additives, alone or in combination, when present in the composition according to the disclosure can be present in a range from about 0.0001% to about 20%, and in some embodiments, from about 0.005% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5%, and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

Methods

The cosmetic compositions of the disclosure are particularly useful in methods for treating the skin, for example, methods for improving the appearance of skin including the skin of the face and/or neck and or around the eyes. In particular, the cosmetic compositions are useful in methods for reducing the appearance of fine lines of the skin; reducing the appearance of wrinkles of the skin; improving the tone of skin and/or improving the evenness of skin tone; improving skin softness and/or smoothness; and/or increasing the radiance, luminosity, and/or glow of the skin. Such methods typically entail topically applying a cosmetically effective amount of the cosmetic composition to the skin, for example, the skin of the face and/or the neck and/or around the eyes. The methods may include one application or multiple applications. For instance, the cosmetic compositions may be applied to the skin (e.g., the face and/or neck) once per week, once every-other-day, once per day, twice per day, or more than twice per day; and the application(s) repeated for a period of time, for example, every-other-day for one or two weeks, every day one week, two weeks, one month, two months, three months, six months, one year, or longer. In some cases, the cosmetic composition is regularly applied to the skin once for an initial period of time followed by regular application for a subsequent second period of time, wherein the regular application during the initial period is less frequent than the regular application during the subsequent second period of time. This allows the skin to adjust gradually to the cosmetic composition. For example, the cosmetic composition may be applied to the skin every-other-day for an initial period of time (e.g., for one week) and subsequently applied to the skin every day for a subsequent second period of time (e.g., for one week, four weeks, eight weeks, or longer).

Implementation of the present disclosure is provided by way of the following examples. The examples serve to illustrate the technology without being limiting in nature. The examples below according to the invention are given by way of illustration and without a limiting nature. The names are the chemical name or the INCI name. The amounts are given therein as % by weight, unless otherwise mentioned.

EXAMPLES

Example 1: Formulations Comprising the Composition

Generally, any composition of the invention can be applied to a keratinous substrate or tissue. For topical application to the skin, the composition can have the form in particular of aqueous water-based formulations.

TABLE 1

Inventive Compositions

| Ingredient | Range |
| --- | --- |
| Acetyl Trifluoromethylphenyl Valylglycine | about 0.5% up to about 2% |
| Hydroxyethyl Urea | about 4% up to about 26.5%, or from about 4.5% to about 18% |
| Optional Ingredients (Thickeners, Surfactants, Humectants, Silicones, Fatty compounds, Actives, pH adjusters, fragrance, chelating agents, antimicrobials, preservatives) | about 0.0001% to about 20% (individually or in combination) |
| Water (optionally with water- based solvent) | about 30% to about 75% |

Referring to Table 1, above, each of the compositions are provided in a cosmetically numbers indicate proportion of ingredients by weight percent based on 100 final weight. Other inventive examples may be formulated in a cosmetically acceptable carrier that includes water and water solvents that are the same or comparable to those listed above in the general amounts as shown, including such other optional additives as may be listed above or mentioned in the description.

In a representative embodiment, identified herein as INVENTIVE 1, the inventive composition according to the disclosure has a pH of about 6 and includes Acetyl Trifluoromethylphenyl Valylglycine (2.00% by weight), Hydroxyethyl Urea (in a range from about 4% to less than 27% by weight, more particularly from about 4% to about 26.5% by weight, most particularly at about 11.7%), and other ingredients including Ethylhexylglycerin, Pentylene Glycol, Carbomer, Methyl Gluceth-20 (2.00% by weight), Sodium Benzoate, Sodium Hydroxide, Phenoxyethanol, Taurine, Adenosine, Hydroxyethylpiperazine Ethane Sulfonic Acid, Niacinamide, and Water (QS).

In a representative embodiment, identified herein as INVENTIVE 2, the inventive composition according to the disclosure has a pH of about 6 and includes Acetyl Trifluoromethylphenyl Valylglycine (2.00% by weight), Hydroxyethyl Urea (in a range from about 4% to less than 27% by weight, more particularly from about 11.7% to about 18% by weight, most particularly at about 17.55%), and other ingredients including Ethylhexylglycerin, Pentylene Glycol, Carbomer, Bis-PEG-18 Methyl Ether Dimethyl Silane (2.00% by weight), Sodium Benzoate, Sodium Hydroxide, Phenoxyethanol, Taurine, Adenosine, Hydroxyethylpiperazine Ethane Sulfonic Acid, Niacinamide, and Water (QS).

In another representative embodiment, the inventive composition according to the disclosure has a pH of about 6 and may include Acetyl Trifluoromethylphenyl Valylglycine (2.00% by weight), Hydroxyethyl Urea (at 11.7% by weight or 23.4% by weight), and other ingredients including one or a combination of Ethylhexylglycerin, Pentylene Glycol, Carbomer, Sodium Benzoate, Sodium Hydroxide, Phenoxyethanol, Taurine, Adenosine, Hydroxyethylpiperazine Ethane Sulfonic Acid, Niacinamide, and Water (QS).

In another representative embodiment, the inventive composition according to the disclosure has a pH of about 4.7 and may include Acetyl Trifluoromethylphenyl Valylglycine (1.00% by weight), Hydroxyethyl Urea (at 23.4% by weight), and other ingredients including one or a combination of Ethylhexylglycerin, Pentylene Glycol, Carbomer, Sodium Benzoate, Sodium Hydroxide, Phenoxyethanol, Taurine, Adenosine, Hydroxyethylpiperazine Ethane Sulfonic Acid, Niacinamide, and Water (QS).

Example 2: Solubility and Stability Studies

Solubility and stability was evaluated over time for a period of 10 days in freeze-thaw cycle testing.

Freeze-thaw cycle testing is a type of stability testing to determine whether a combination will remain stable. It entails subjecting the compositions to a series of extreme, rapid temperature changes. The freeze-thaw testing was conducted by exposing the combinations to freezing temperatures (approximately −20° C.±2° C.) for 24 hours. The combinations were then maintained at a higher temperature (approximately 20° C.±2° C.) for 24 hours over a period of 10 days. The combinations were visually analyzed for phase separation and crystallization of the acetyl trifluoromethylphenyl valylglycine. Results are shown in Table 2.

TABLE 2

STABILITY TEST RESULTS

| TEST COMPOSITIONS | STABILITY RESULT |
|---|---|
| INVENTIVE 1<br>2% ACETYL TRIFLUOROMETHYLPHENYL VALYLGLYCINE<br>11.7% HYDROXYETHYL UREA, pH ~6 | PASS |
| INVENTIVE 2<br>2% ACETYL TRIFLUOROMETHYLPHENYL VALYLGLYCINE<br>17.55% HYDROXYETHYL UREA, pH ~6 | PASS |
| COMPARATIVE 1 (INVENTIVE 1 WITHOUT HYDROXYETHYL UREA) | FAIL |
| INVENTIVE 1 with 4.5% HYDROXYETHYL UREA, pH ~6 | PASS |
| INVENTIVE 1 with 18% HYDROXYETHYL UREA, pH ~6 | PASS |
| COMPARATIVE 2 (INVENTIVE 1 with 27% HYDROXYETHYL UREA) | FAIL |
| COMPARATIVE 3 (INVENTIVE 1 with 3% ACETYL TRIFLUOROMETHYLPHENYL VALYLGLYCINE) | FAIL |
| COMPARATIVE 4 - 2% ACETYL TRIFLUOROMETHYLPHENYL VALYLGLYCINE and 23.4% HYDROXYETHYL UREA, pH ~4.7 | FAIL |
| INVENTIVE 3 - 1% ACETYL TRIFLUOROMETHYLPHENYL VALYLGLYCINE and 23.4% HYDROXYETHYL UREA, pH ~4.7 | PASS |

The data show that a water-based composition in a cosmetically acceptable carrier that includes acetyl trifluoromethylphenyl valylglycine stabilized by inclusion of hydroxyethyl urea in the absence of other solvents maintains stability as evidenced by a lack of crystal formation that is visible to the naked eye, and a lack of visually perceptible crystal formation over 10 days of freeze thaw cycles from −20° C. through 20° C. ("PASS"). The comparative compositions that either lack hydroxyethyl urea or in which the hydroxyethyl urea is present at 60% or in which the acetyl trifluoromethylphenyl valylglycine is present above 2% do not demonstrate stability as evidenced by crystal formation that is visible to the naked eye ("FAIL"). The results show that at increased amounts of acetyl trifluoromethylphenyl valylglycine the composition is stabilized with increased pH to a pH of about 6. In some embodiments, stable compositions further demonstrate no perceptible crystal formation after ten days at freeze thaw temperatures that may range from −15° C. to 25° C., or a range or subrange therein, or over a period of time up to eight (8) weeks at an ambient temperature from about 25° C. up to about 37° C., or combinations thereof. In some embodiments the composition may demonstrate stability when crystals are visualized at a temperature at or below 4° C., such crystals disappear with or without mild agitation within 24 hours of reaching an ambient temperature from about 25° C. up to about 37° C., or after freeze thaw cycles from −20° C. through 20° C., or from −15° C. through 25° C. In some embodiments, the composition may demonstrate stability for a period of time up to eight (8) weeks.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more than one, including two or more than two, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.5% by weight, less than about 0.1% by weight, less than about 0.05% by weight, or less than about 0.01% by weight, or none of the specified material, all amounts based on the total weight of the composition. All elements positively set forth in the instant disclosure can be negatively excluded, i.e., the compositions of methods can be "free," "substantially free," or "essentially free" of any of the elements positively set forth herein.

The term "about," means within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. A range given of "about 1% to 10%" is intended to have the term "about" modifying both the 1% and the 10% endpoints. Further, a range is intended to be inclusive of the endpoints of and all numbers in the range except as expressly stated otherwise. Further still, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A water-based cosmetic composition comprising:
   (a) acetyl trifluoromethylphenyl valylglycine, present from 0.5% and up to about 2%;
   (b) hydroxyethyl urea present from about 4.5% to about 23.4%;
   (c) a cosmetically acceptable carrier comprising water; and
   (d) optionally, one or more additives wherein:
   for a concentration of acetyl trifluoromethylphenyl valylglycine from 0.5% and up to 1%, the composition has a pH from about 4.5 to 5;
   for a concentration of acetyl trifluoromethylphenyl valylglycine above 1% and up to 2%, the composition has a pH greater than 5 and up to about 6.5; and
   the composition includes not more than one ingredient selected from the group consisting of ethoxydiglycol, dimethyl isosorbide, triethyl citrate, isopropyl lauryl sarcosinate, propylene glycol, and propanediol; and
   all weight percentages are based on the total weight of the cosmetic composition.

2. The water-based cosmetic composition according to claim 1, wherein the composition demonstrates stability as evidenced by a lack of crystal formation that is visible to the naked eye, and a lack of visually perceptible crystal formation at an ambient temperature from about 25° C. up to about 37° C. and after freeze thaw cycles from −20° C. through 20° C.

3. The water-based cosmetic composition according to claim 1, wherein the composition demonstrates stability when crystals are visualized at a temperature at or below 4° C., such crystals disappear with or without mild agitation within 24 hours of reaching an ambient temperature from about 25° C. up to about 37° C. and after freeze thaw cycles from −20° C. through 20° C.

4. The water-based cosmetic composition according to claim 1, wherein the composition includes:
   (a) the acetyl trifluoromethylphenyl valylglycine present at about 2%, by weight of the composition;
   (b) the hydroxyethyl urea present from about 11.7% and up to about 18%, by weight of the composition;
   (c) the cosmetically acceptable carrier present from about 30% to about 70%, by weight of the composition; and
   (d) the other optional ingredients present from about 0.001% to about 20%, by weight of the composition, wherein the composition has a pH of about 6.

5. The water-based cosmetic composition according to claim 1, wherein the composition includes:
   (a) the acetyl trifluoromethylphenyl valylglycine present at about 1%, by weight of the composition;
   (b) the hydroxyethyl urea present at about 23.4%, by weight of the composition;
   (c) the cosmetically acceptable carrier present from about 30% to about 70%, by weight of the composition; and
   (d) the other optional ingredients present from about 0.001% to about 20%, by weight of the composition, wherein the composition has a pH of about 4.7.

6. The water-based cosmetic composition according to claim 1, wherein water is present from about 10% to about 75%, by weight of the composition.

7. The water-based cosmetic composition according to claim 1, wherein the one or more optional ingredients is selected from the group consisting of fatty compound(s); thickening agent(s); surfactants; other additives and skin active agent(s); and combinations of the foregoing.

8. The water-based cosmetic composition according to claim 1, wherein the one or more optional additives is selected from the group consisting of pH adjusters, chelating agents, skin care actives, preservatives, fillers, powders, fragrances, dyes, pigments, and combinations thereof.

9. The water-based cosmetic composition according to claim 1, wherein the one or more optional additives is selected from the group consisting of ethylhexylglycerin, pentylene glycol, carbomer, methyl gluceth-20, Bis-PEG-18 methyl ether dimethyl silane, sodium benzoate, sodium hydroxide, phenoxyethanol, taurine, adenosine, hydroxyethylpiperazine ethane sulfonic acid, niacinamide, and combinations thereof.

10. The water-based cosmetic composition according to claim 1, wherein the one or more optional additives comprises ethylhexylglycerin, pentylene glycol, carbomer, methyl gluceth-20, sodium benzoate, sodium hydroxide, phenoxyethanol, taurine, adenosine, hydroxyethylpiperazine ethane sulfonic acid, and niacinamide.

11. The water-based cosmetic composition according to claim 1, wherein the one or more optional additives comprises ethylhexylglycerin, pentylene glycol, carbomer, Bis-PEG-18 methyl ether dimethyl silane, sodium benzoate, sodium hydroxide, phenoxyethanol, taurine, adenosine, hydroxyethylpiperazine ethane sulfonic acid, and niacinamide.

12. The water-based cosmetic composition according to claim 1, comprising methyl gluceth-20.

13. The water-based cosmetic composition according to claim 1, comprising Bis-PEG-18 methyl ether dimethyl silane.

14. The water-based cosmetic composition according to claim 1, wherein the composition is monophasic and essentially free of oil.

15. The water-based cosmetic composition according to claim 1, wherein the composition excludes one or more ingredients selected from the group consisting of water-soluble solvents selected from the group consisting of monoalcohols and polyols, diols, glycols, glycol ethers and combinations thereof.

16. The water-based cosmetic composition according to claim 1, wherein the composition excludes ethoxydiglycol, dimethyl isosorbide, triethyl citrate, isopropyl lauryl sarcosinate, propylene glycol, and propanediol.

17. The water-based cosmetic composition according to claim 1, wherein the composition excludes or is essentially free from ingredients selected from the group consisting of parabens, phthalates, cyclomethicones, fragrance, silicone, mineral oil, synthetic dyes, gelling agents, sulfates, polyquaternium, microplastics, EDTA, silicone oils, mineral UV filter agents, organic UV filter agents, and combinations thereof.

18. The water-based cosmetic composition according to claim 1, wherein the composition is free from petroleum-based ingredients.

19. A water-based cosmetic composition, comprising:
(a) acetyl trifluoromethylphenyl valylglycine, present at about 2%;
(b) hydroxyethyl urea present from about 4.5% to about 18%;
(c) a cosmetically acceptable carrier comprising water; and
(d) optionally, one or more additives one or more additives wherein all weight percentages are based on the total weight of the cosmetic composition, and wherein the composition has a pH in a range from greater than 5 and up to about 6.5, wherein the composition demonstrates stability as evidenced by a lack of crystal formation that is visible to the naked eye, and a lack of visually perceptible crystal formation at an ambient temperature from about 25° C. up to about 37° C. and after freeze thaw cycles from −20° C. through 20° C., and wherein the composition includes not more than one ingredient selected from the group consisting of ethoxydiglycol, dimethyl isosorbide, triethyl citrate, isopropyl lauryl sarcosinate, propylene glycol, and propanediol.

20. A water-based cosmetic composition, comprising:
(a) acetyl trifluoromethylphenyl valylglycine, present at about 2%;
(b) hydroxyethyl urea present from about 4.5% to about 18%;
(c) a cosmetically acceptable carrier comprising water; and
(d) optionally, one or more additives comprising methyl gluceth-20 or Bis-PEG-18 methyl ether dimethyl silane wherein all weight percentages are based on the total weight of the cosmetic composition, and wherein the composition has a pH in a range from greater than 5 and up to about 6.5, and wherein the composition demonstrates stability as evidenced by a lack of crystal formation that is visible to the naked eye, and a lack of visually perceptible crystal formation at an ambient temperature from about 25° C. up to about 37° C. and after freeze thaw cycles from −20° C. through 20° C., and wherein the composition excludes ethoxydiglycol, dimethyl isosorbide, triethyl citrate, isopropyl lauryl sarcosinate, propylene glycol, propanediol.

* * * * *